(12) United States Patent
Quillin

(10) Patent No.: US 8,202,654 B2
(45) Date of Patent: Jun. 19, 2012

(54) MEDICAL DEVICES HAVING FLUOROCARBON POLYMER COATINGS

(75) Inventor: Daniel Quillin, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 399 days.

(21) Appl. No.: 12/491,528

(22) Filed: Jun. 25, 2009

(65) Prior Publication Data

US 2009/0326647 A1    Dec. 31, 2009

Related U.S. Application Data

(60) Provisional application No. 61/075,769, filed on Jun. 26, 2008.

(51) Int. Cl.
*H01M 2/16* (2006.01)

(52) U.S. Cl. ........ 429/246; 424/422; 428/461; 623/1.49

(58) Field of Classification Search .................. 429/246; 428/461; 424/422; 623/1.49
See application file for complete search history.

(56) References Cited

U.S. PATENT DOCUMENTS

| | | | |
|---|---|---|---|
| 6,387,379 B1 | 5/2002 | Goldberg et al. | |
| 6,545,097 B2 | 4/2003 | Pinchuk et al. | |
| 6,746,773 B2 | 6/2004 | Llanos et al. | |
| 8,021,676 B2* | 9/2011 | Pacetti et al. | 424/423 |
| 2003/0236514 A1 | 12/2003 | Schwarz | |
| 2004/0063805 A1 | 4/2004 | Pacetti et al. | |
| 2005/0069778 A1* | 3/2005 | Bonnet et al. | 429/246 |
| 2005/0106204 A1 | 5/2005 | Hossainy et al. | |
| 2005/0118372 A1 | 6/2005 | Bonnet et al. | |
| 2005/0159558 A1* | 7/2005 | Govaerts et al. | 525/326.3 |
| 2005/0170121 A1 | 8/2005 | Bonnet et al. | |
| 2006/0129216 A1* | 6/2006 | Hastings et al. | 607/115 |
| 2006/0134165 A1 | 6/2006 | Pacetti et al. | |
| 2006/0222756 A1 | 10/2006 | Davila et al. | |
| 2008/0004695 A1 | 1/2008 | Stewart et al. | |

FOREIGN PATENT DOCUMENTS

| | | | |
|---|---|---|---|
| WO | 2008021948 A2 | 2/2008 | |
| WO | WO-2008/021948 A2 * | 2/2008 | |
| WO | WO-2009/158485 A2 * | 12/2009 | |

OTHER PUBLICATIONS

Technical Polymers, 1 page, downloaded from http://www.arkema-inc.com/index.cfm?pag=1050 on Jan. 16, 2008.

(Continued)

*Primary Examiner* — Peter D. Mulcahy
*Assistant Examiner* — Henry Hu
(74) *Attorney, Agent, or Firm* — Mayer & Williams PC; David B. Bonham; Keum J. Park

(57) ABSTRACT

In accordance with various aspects of the invention, implantable and insertable medical devices are provided, which contain (a) a substrate and (b) a polymeric layer disposed on the substrate that comprises a fluorinated polymer to which is grafted an unsaturated monomer having at least one carbon double bond and at least one polar functional group.

20 Claims, 1 Drawing Sheet

OTHER PUBLICATIONS

Kynar® ADX, 1 page, downloaded from http://www.arkema-inc.com/index.cfm?pag=1049 on Jan. 16, 2008.
Kynar® ADX 111: new adhesive PVDF grade for powder coatings, May 15, 2006, 1 page.
Kynar® PVDF, Resins for Battery Manufacture, 2007, 4 pp.
S.V. Ranade et al., "Styrenic block copolymers for biomaterial and drug delivery applications," Acta Biomater 1, 2005, 137-44.
R. Virmani et al., "Localized Hypersensitivity and late Coronary Thrombosis Secondary to a Sirolimus-Eluting Stent," Circulation 2004 109(6) 701-705.
Ranade et al., "Physical characterization of controlled release of paclitaxel from the TAXUS™ Express2™ drug-eluting stent," J Biomed Mater Res 71A: 2004, 625-634.

* cited by examiner

MEDICAL DEVICES HAVING FLUOROCARBON POLYMER COATINGS

FIELD OF THE INVENTION

The present invention relates generally to medical devices, and more particularly to implantable or insertable medical devices.

BACKGROUND OF THE INVENTION

The implantation or insertion of medical devices into the body of a patient is common in the practice of modern medicine. For instance, over the past few years, stents (i.e., devices which are expanded inside blood vessels to increase blood flow in areas blocked by plaque) have emerged as a prime therapy for atherosclerosis. Unfortunately, in-stent restenosis may occur in some instances (e.g., as a result of injury to the vessel wall). Drug eluting stents have a polymeric coating over the stent to release a drug at a prescribed rate for a given duration to counteract the effects of in-stent restenosis. The coating on the stent is in contact with the delivery system (e.g., balloon) along its inner diameter and in contact with the vessel wall along its outer diameter. Examples of drug eluting coronary stents include commercially available stents from Boston Scientific Corp. (TAXUS, PROMUS), Johnson & Johnson (CYPHER), and others. See S. V. Ranade et al., *Acta Biomater.* 2005 January; 1(1): 137-44 and R. Virmani et al., *Circulation* 2004 Feb. 17, 109(6) 701-5.

Various types of polymeric materials have been used as drug-releasing reservoirs, including, for example, homopolymers such as poly(n-butyl methacrylate) and copolymers such as poly(ethylene-co-vinyl acetate), poly(isobutylene-co-styrene), for example, poly(styrene-b-isobutylene-b-styrene) triblock copolymers (SIBS), described, for instance, in U.S. Pat. No. 6,545,097 to Pinchuk et al., and poly(vinylidene fluoride-co-hexafluoropropylene), described, for instance, in Pub. No. US 2008/0004695 to Stewart et al.

SUMMARY OF THE INVENTION

In accordance with various aspects of the invention, implantable and insertable medical devices are provided, which contain (a) a substrate and (b) a polymeric layer disposed on the substrate that comprises a fluorinated polymer to which is grafted at least one type of unsaturated monomer, which monomer has at least one carbon double bond and at least one polar functional group.

An advantage of the present invention is that polymeric layers may be provided, which adhere well to underlying substrate materials, including metallic materials.

These and other aspects, embodiments and advantages of the present invention will become immediately apparent to those of ordinary skill in the art upon review of the Detailed Description and any claims to follow.

DETAILED DESCRIPTION OF THE INVENTION

Figure 1A:
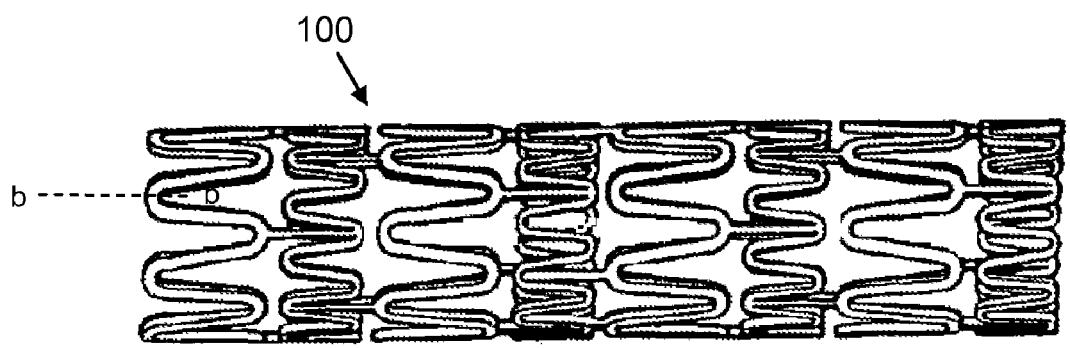
FIG. 1A is a schematic view of a stent, in accordance with an embodiment of the present invention.

A more complete understanding of the present invention is available by reference to the following detailed description of numerous aspects and embodiments of the invention. The detailed description of the invention which follows is intended to illustrate but not limit the invention.

In accordance with various aspects of the invention, implantable and insertable medical devices are provided, which contain (a) a substrate and (b) a polymeric layer disposed on the substrate that comprises a fluorinated polymer to which is grafted at least one type of unsaturated monomer, which monomer has at least one carbon double bond and at least one polar functional group.

Such layers can be provided over the underlying substrate at a variety of locations and in a variety of shapes (e.g., in the form of a series of rectangles, stripes, or any other continuous or non-continuous pattern). As used herein a "layer" of a given material is a region of that material whose thickness is small compared to both its length and width. As used herein a layer need not be planar, for example, taking on the contours of an underlying substrate. Layers can be discontinuous (e.g., patterned).

Examples of implantable or insertable medical devices upon which layers in accordance with the present invention may be formed include, for example, stents (including coronary vascular stents, peripheral vascular stents such as cerebral stents, urethral, ureteral, biliary, tracheal, gastrointestinal and esophageal stents), stent grafts, vascular grafts, abdominal aortic aneurysm (AAA) devices (e.g., AAA stents, AAA grafts, etc.), vascular access ports, dialysis ports, embolization devices including cerebral aneurysm filler coils (including Guglilmi detachable coils and metal coils), myocardial plugs, septal defect closure devices, patches, catheters (e.g., renal or vascular catheters including balloon catheters), guide wires, balloons, filters (e.g., vena cava filters and mesh filters for distal protection devices), pacemakers, leads, including lead coatings such as coatings for pacemaker leads, defibrillation leads and coils, ventricular assist devices including left ventricular assist hearts and pumps, total artificial hearts, shunts, valves including heart valves and vascular valves, anastomosis clips and rings, cochlear implants, tissue bulking devices, tissue engineering scaffolds for cartilage, bone, skin and other in vivo tissue regeneration, tissue staples and ligating clips at surgical sites, cannulae, metal wire ligatures, urethral slings, hernia "meshes", artificial ligaments, joint prostheses, orthopedic prosthesis such as bone grafts, bone plates, fins and fusion devices, orthopedic fixation devices such as interference screws in the ankle, knee, and hand areas, tacks for ligament attachment and meniscal repair, rods and pins for fracture fixation, screws and plates for craniomaxillofacial repair, and dental devices such as dental implants, as well as various other substrates (which can be, for example, metallic, polymeric and/or ceramic, etc.) which have disposed thereon layers in accordance with the invention and which are implanted or inserted into the body.

Substrate materials for the medical devices of the present invention may vary widely in composition and are not limited to any particular material. They can be selected from a range of biostable materials and biodisintegrable materials (i.e., materials that are dissolved, degraded, resorbed, or otherwise eliminated upon placement in the body), including (a) organic materials (i.e., materials containing organic species, typically 50 wt % or more) such as polymeric materials (i.e., materials containing polymers, typically 50 wt % or more polymers) and biologics, (b) inorganic materials (i.e., materials containing inorganic species, typically 50 wt % or more), such as metallic materials (i.e., materials containing metals, typically 50 wt % or more) and non-metallic inorganic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others), and (c) hybrid materials (e.g., hybrid organic-inorganic materials, for instance, polymer/metallic inorganic and polymer/non-metallic inorganic hybrids).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals such as gold, silver, iron, nickel, copper, aluminum, niobium, platinum, palladium, iridium, osmium, rhodium, titanium, tantalum, tungsten, ruthenium, zinc and magnesium, among others, and alloys such as those comprising iron and chromium (e.g., stainless steels, including platinum-enriched radiopaque stainless steel), niobium alloys, tantalum alloys, titanium alloys, including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium, zinc and/or iron (and their alloys with combinations of one another and with Ce, Ca, Zr and Li), among others.

Specific examples of organic materials include a wide variety of biostable and biodisintegrable polymers, along with other high molecular weight organic materials.

As used herein, a "polymeric" material is one that contains polymers, for example, from 50 wt % or less to 75 wt % to 90 wt % to 95 wt % to 97.5 wt % to 99 wt % or more polymers.

As used herein, "polymers" are molecules containing multiple copies (e.g., from 5 to 10 to 25 to 50 to 100 to 250 to 500 to 1000 or more copies) of one or more constitutional units, commonly referred to as monomers. As used herein, the term "monomers" may refer to the free monomers and to those that have been incorporated into polymers, with the distinction being clear from the context in which the term is used.

Polymers may take on a number of configurations, which may be selected, for example, from linear, cyclic and branched configurations, among others. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit (i.e., monomer). "Copolymers" are polymers that contain multiple copies of at least two dissimilar constitutional units, examples of which include random, statistical, gradient, periodic (e.g., alternating) and block copolymers.

As previously noted, medical devices in accordance with the invention contain (a) a substrate and (b) a polymeric layer disposed on the substrate that comprises a fluorinated polymer to which is grafted at least one type of unsaturated monomer, which has at least one carbon double bond and at least one polar functional group (referred to herein as a "monomer-grafted fluorinated polymer"). Such grafted monomers may be provided to enhance the adhesion of the polymeric layer to the substrate, among other effects.

Fluorinated polymers in accordance with the invention include fluorinated homopolymers and fluorinated copolymers comprising one or more fluorinated alkene monomers (which consist of carbon, fluorine and optionally hydrogen), such as vinyl fluoride, vinylidene fluoride, trifluoroethylene, tetrafluoroethylene, and hexafluoropropylene, among others. A specific example of a fluorinated homopolymer is polyvinylidene fluoride (PVDF). A specific example of a fluorinated copolymer is poly(vinylidene fluoride-co-hexafluoropropylene) (PVDF-HFP).

Monomers which may be grafted to the fluorinated polymer include unsaturated monomers having at least one carbon double bond and one, two, three or more polar functional groups, for example, selected from the following polar functional groups: carboxylic acid groups, carboxylic acid salt groups, carboxylic acid anhydride groups, epoxide groups, carboxylic acid ester groups, silyl groups, carboxylic amide groups, hydroxyl groups, and isocyanate groups. Specific examples include, for instance, methacrylic acid, acrylic acid, maleic acid, fumaric acid, itaconic acid, citraconic acid, undecylenic acid, allylsuccinic acid, cyclohex-4-ene-1,2-dicarboxylic acid, 4-methylcyclohex-4-ene-1,2-dicarboxylic acid, bicyclo[2.2.1]hept-5-ene-2,3-dicarboxylic acid, x-methylbicyclo-[2.2.1]hept-5-ene-2,3-dicarboxylic acid, salts of the foregoing acids (e.g., sodium, potassium, calcium, magnesium, zinc, etc.), maleic anhydride, itaconic anhydride, citraconic anhydride, dichloromaleic anhydride, difluoromaleic anhydride, crotonic anhydride, glycidyl acrylate, glycidyl methacrylate, allyl glycidyl ether and vinylsilanes, such as vinyltrimethoxysilane, vinyltriethoxysilane, vinyltriacetoxysilane and gamma-methacryloxypropyltrimethoxysilane. Unsaturated dicarboxylic acids having 4 to 10 carbon atoms and their salts and anhydrides are preferred grafting monomers in some instances.

Grafting may be done by blending the fluoropolymer and monomer, followed by irradiation (e.g., gamma irradiation) of the blend. In certain embodiments, maleic-anhydride-grafted vinylidene fluoride polymers may be formed as described in Pub. Nos. US 2005/0118372, US 2005/0170121 and US 2005/0069778, all to Bonnet et al. In brief, a blend of maleic anhydride and a vinylidene fluoride polymer (e.g., PVDF or PVDF-HFP) is prepared in a twin-screw extruder. The blend is then bagged in a sealed aluminum-lined bag, and oxygen is removed by flushing with argon. The bag is then irradiated with gamma irradiation (e.g., 3-5 Mrad by means of a cobalt 60 bomb).

Maleic-anhydride-grafted polyvinylidene fluoride is also commercially available from Arkema, Inc., Philadelphia, Pa., USA, as Kynar® ADX and Kynar® ADX 111.

In certain embodiments, in addition to a monomer-grafted fluorinated polymer, polymeric layers in accordance with the present invention may optionally contain a non-grafted fluorinated polymer. A non-grafted fluorinated polymer may be added, for example, to modify the release profile of an optional therapeutic agent that is contained within the layer, among other purposes. For instance, in some embodiments, layers may be formed that contain the following: (a) a combination of PVDF and maleic-anhydride-grafted PVDF, (b) a combination of PVDF-HFP and maleic-anhydride-grafted PVDF or (c) a combination of PVDF-HFP and maleic-anhydride-grafted PVDF-HFP, among numerous other possibilities.

In certain embodiments, an additional polymeric layer is provided over the layer that comprises the monomer-grafted fluorinated polymer. For example, the additional layer may be formed from one or more non-grafted fluorinated polymers, in which case the underlying layer that comprises the monomer-grafted fluorinated polymer may act as a tie layer for the additional layer. For instance, in some embodiments, devices may be formed that contain the following: (a) a layer containing PVDF over a layer containing maleic-anhydride-grafted PVDF, (b) a layer containing PVDF-HFP over a layer containing maleic-anhydride-grafted PVDF or (c) a layer containing PVDF-HFP over a layer containing maleic-anhydride-grafted PVDF-HFP, among numerous other possibilities.

In addition to one or more polymers, the polymeric layers for use in the medical devices of the present invention may optionally contain one or more therapeutic agents. "Therapeutic agents," "drugs," "pharmaceutically active agents," "pharmaceutically active materials," and other related terms may be used interchangeably herein. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Figure 1B:
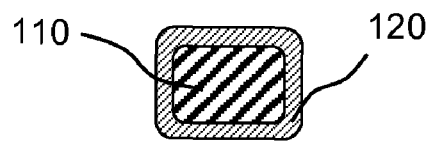
FIG. 1B is schematic view of a cross section taken along line b-b of FIG. 1A, in accordance with an embodiment of the present invention.

Several specific embodiments of the invention will now be described with reference to the Figures. Referring now to FIGS. 1A and 1B, a stent 100 is shown, in accordance with an embodiment of the present invention. As seen from FIG. 1B, which is a cross section taken along line b-b of FIG. 1A, the stent 100 comprises a substrate 110, which may be, for example, a biostable metallic substrate such as a nitinol or stainless steel substrate or a bioresorbable metallic substrate such as iron, magnesium, zinc or their alloys, among others. The coating 120 contains a monomer-grafted fluorinated polymer, in accordance with the invention, and may also optionally contain a non-grafted fluorinated polymer and/or a therapeutic agent in certain embodiments.

Figure 2:
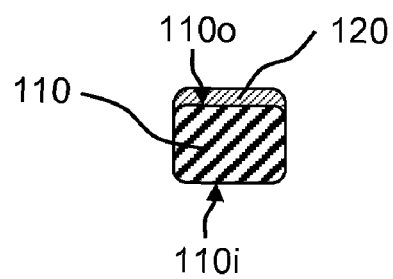
FIG. 2 is an alternative schematic view of a cross section taken along line b-b of FIG. 1A, in accordance with another embodiment of the present invention.

FIG. 2, which is an alternative cross section taken along line b-b of FIG. 1A, shows a coating 120, which is disposed on the outer abluminal (e.g., blood vessel contacting) surface 110o of the substrate 110 but not on the inner luminal (e.g., blood contacting surface) surface 110i of the substrate 110. As above, the coating 120 contains a monomer-grafted fluorinated polymer, in accordance with the invention, which as noted previously may be used to enhance adhesion to the substrate 110. The coating 120 may also optionally contain a non-grafted fluorinated polymer and/or a therapeutic agent in certain embodiments. In a specific embodiment where the coating 120 contains an antirestenotic agent, agent delivery is targeted to the blood vessel wall, where the restenosis occurs. While the coating of FIG. 2 is shown on the abluminal surface, it should be understood that coatings in accordance with the present invention may be provide on any surface. For example, it may be desirable to provide a coating on the luminal surface, which coating contains a monomer-grafted fluorinated polymer, an optional non-grafted fluorinated polymer, and an optional therapeutic agent (e.g., an antithrombotic agent, among many others).

Figure 3:
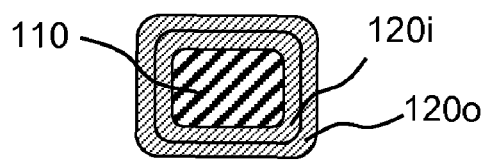
FIG. 3 is an alternative schematic view of a cross section taken along line b-b of FIG. 1A, in accordance with yet another embodiment of the present invention.

FIG. 3, which is an additional alternative cross section taken along line b-b of FIG. 1A, shows an inner coating layer 120i disposed on the substrate and an outer coating layer 120o disposed on the inner coating layer coating 120i. The inner coating 120i may contain, for example, a monomer-grafted fluorinated polymer, in accordance with the invention, and may be used to enhance adhesion to the substrate 110. The outer coating 120o may contain, for example, a non-grafted fluorinated polymer and a therapeutic agent in certain embodiments. In certain embodiments, FIG. 3 may be modified such that the inner and outer coatings are provided only on the abluminal surface of the substrate (see FIG. 2) or only on the luminal surface, among other possibilities.

Numerous techniques are available for forming polymeric layers in accordance with the present invention.

For example, where a polymeric layer is formed from one or more polymers having thermoplastic characteristics, a variety of standard thermoplastic processing techniques may be used to form the polymeric layer. Using these techniques, a polymeric layer can be formed, for instance, by (a) first providing a melt that contains polymer(s) and any other optional agents such as therapeutic agents, and (b) subsequently cooling the melt. Examples of thermoplastic processing techniques include compression molding, injection molding, blow molding, spraying, vacuum forming and calendaring, extrusion into sheets, fibers, rods, tubes and other cross-sectional profiles of various lengths, and combinations of these processes.

Other processing techniques besides thermoplastic processing techniques may also be used to form the polymeric layers of the present invention, including solvent-based techniques. Using these techniques, polymeric layers can be formed, for instance, by (a) first providing a solution or dispersion that contains polymer(s) and any optional agents such as therapeutic agents and (b) subsequently removing the solvent. The solvent that is ultimately selected will contain one or more solvent species, which are generally selected based on their ability to dissolve at least one of the polymer(s) that form the polymeric layer, in addition to other factors, including drying rate, surface tension, etc. Examples of solvents may be selected from N-methyl-2-pyrrolidone (NMP) or another solvent such as dimethyl formamide (DMF), dimethyl acetamide (DMAC), tetramethyl urea, dimethyl sulfoxide (DMSO) and/or triethyl phosphate, among others. For these and other suitable solvents, see, e.g., "Kynar® PVDF Resins For Battery Manufacture" available from Arkema, Inc., Philadelphia, Pa., USA. In certain embodiments, the solvent is selected based on its ability to dissolve the optional agents, if any (e.g., paclitaxel, among many other therapeutic agents, is soluble in DMF, among many other solvents). Thus, optional agents such as therapeutic agents may be dissolved or dispersed in the coating solution. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, brushing techniques, stamping techniques, rolling techniques, electrostatic techniques, and combinations of these processes.

In many embodiments of the invention, a polymer containing solution (where solvent-based processing is employed) or a polymer containing melt (where thermoplastic processing is employed) is applied to a substrate to form a polymeric layer. For example, the substrate can correspond to all or a portion of an implantable or insertable medical device to which a polymeric coating is applied, for example, by spraying, extrusion, and so forth. In other embodiments, for example, extrusion and co-extrusion techniques, one or more polymeric layers are formed without the aid of a pre-existing substrate. In a specific example, a polymeric layer may be co-extruded along with an underlying substrate material.

As previously indicated, layers in accordance with the invention may optionally include one or more therapeutic agents.

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists.

Numerous therapeutic agents, not necessarily exclusive of those listed above, have been identified as candidates for vascular treatment regimens, for example, as agents targeting restenosis (antirestenotic agents). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK (D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein), SOD mimics, verteporfin, rostaporfin, AGI 1067 and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline, and (dd) glucose cross-link breakers such as alagebrium chloride (ALT-711).

Preferred therapeutic agents in some embodiments include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the foregoing, among others.

A wide range of therapeutic agent loadings may be used in conjunction with the medical devices of the present invention. Typical loadings range, for example, from than 1 wt % or less to 2 wt % to 5 wt % to 10 wt % to 25 wt % or more of the polymeric layer.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising (a) an inorganic substrate, (b) a first layer disposed on the substrate, said first layer comprising a first fluorinated polymer to which is grafted at least one type of unsaturated monomer, said monomer comprising one carbon-carbon double bond and a polar functional group, and (c) a second layer disposed on the first layer, said second layer comprising a non-grafted fluorinated polymer and a therapeutic agent.

2. The medical device of claim 1, wherein the first fluorinated polymer is a vinylidene fluoride polymer.

3. The medical device of claim 2, wherein the vinylidene fluoride polymer is selected from polyvinylidene fluoride and poly(vinylidene fluoride-co-hexafluoropropylene).

4. The medical device of claim 1, wherein the unsaturated monomer is an unsaturated dicarboxylic acid, unsaturated dicarboxylic acid salt, or unsaturated acid anhydride having from 4 to 10 carbon atoms.

5. The medical device of claim 1, wherein the unsaturated monomer is maleic anhydride.

6. The medical device of claim 5, wherein the first layer comprises maleic-anhydride-grafted polyvinylidene fluoride, maleic-anhydride-grafted poly(vinylidene fluoride-co-hexafluoropropylene), or a combination thereof.

7. The medical device of claim 1, wherein the non-grafted fluorinated polymer is a non-grafted vinylidene fluoride polymer.

8. The medical device of claim 7, wherein the non-grafted vinylidene fluoride polymer is selected from polyvinylidene fluoride, poly(vinylidene fluoride-co-hexafluoropropylene), and combinations thereof.

9. The medical device of claim 1, wherein the medical device is a stent.

10. The medical device of claim 2, wherein the medical device is a stent.

11. The medical device of claim 10, wherein the therapeutic agent is an antirestenotic agent.

12. The medical device of claim 10, wherein the first layer is applied to the abluminal surface of the stent but not the luminal surface of the stent.

13. The medical device of claim 2, wherein the unsaturated monomer is an unsaturated dicarboxylic acid, unsaturated dicarboxylic acid salt, or unsaturated acid anhydride having from 4 to 10 carbon atoms.

14. The medical device of claim 2, wherein the unsaturated monomer is maleic anhydride.

15. The medical device of claim 14, wherein the first layer comprises maleic-anhydride-grafted polyvinylidene fluoride, maleic-anhydride-grafted poly(vinylidene fluoride-co-hexafluoropropylene), or a combination thereof.

16. The medical device of claim 2, wherein the non-grafted fluorinated polymer is a non-grafted vinylidene fluoride polymer.

17. The medical device of claim 16, wherein the non-grafted vinylidene fluoride polymer is selected from polyvinylidene fluoride, poly(vinylidene fluoride-co-hexafluoropropylene), and combinations thereof.

18. The medical device of claim 1, wherein said inorganic substrate is selected from a metal substrate and a metal alloy substrate.

19. The medical device of claim 2, wherein said inorganic substrate is selected from a metal substrate and a metal alloy substrate.

20. An implantable or insertable medical device comprising (a) an inorganic substrate selected from a metal substrate and a metal alloy substrate, (b) a first layer disposed on the substrate, said first layer comprising a vinylidene fluoride polymer to which is grafted at least one type of unsaturated monomer, said unsaturated monomer comprising one carbon-carbon double bond and a polar functional group, and (c) a second layer disposed on the first layer, said second layer comprising a non-grafted vinylidene fluoride polymer and a therapeutic agent.

* * * * *